(12) United States Patent
Dalko

(10) Patent No.: US 9,138,389 B2
(45) Date of Patent: Sep. 22, 2015

(54) USE OF A JASMONIC ACID COMPOUND FOR TREATING GREASY SKIN

(75) Inventor: Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 354 days.

(21) Appl. No.: 13/378,837

(22) PCT Filed: Jul. 1, 2010

(86) PCT No.: PCT/FR2010/051372
§ 371 (c)(1),
(2), (4) Date: Dec. 16, 2011

(87) PCT Pub. No.: WO2011/001111
PCT Pub. Date: Jan. 6, 2011

(65) Prior Publication Data
US 2012/0088836 A1    Apr. 12, 2012

Related U.S. Application Data

(60) Provisional application No. 61/224,080, filed on Jul. 9, 2009.

(30) Foreign Application Priority Data

Jul. 2, 2009  (FR) ..................... 09 54529

(51) Int. Cl.
*A01N 37/08* (2006.01)
*A01N 53/00* (2006.01)
*A61K 31/19* (2006.01)
*A61K 31/557* (2006.01)
*A61K 8/36* (2006.01)
*A61K 8/365* (2006.01)
*A61K 8/37* (2006.01)
*A61Q 19/00* (2006.01)

(52) U.S. Cl.
CPC . *A61K 8/36* (2013.01); *A61K 8/365* (2013.01); *A61K 8/37* (2013.01); *A61Q 19/008* (2013.01)

(58) Field of Classification Search
USPC ......................................................... 514/573
See application file for complete search history.

(56) References Cited

U.S. PATENT DOCUMENTS

| 2004/0029839 A1* | 2/2004 | Boulle et al. ............... 514/129 |
| 2004/0185075 A1* | 9/2004 | Dalko ....................... 424/401 |
| 2006/0110475 A1 | 5/2006 | Schwaller |

FOREIGN PATENT DOCUMENTS

| EP | 1 333 021 | 8/2003 |
| JP | 10029935 | 2/1998 |
| WO | 2004 023897 | 3/2004 |

OTHER PUBLICATIONS

"Matipure: Sebum Exchanger—A Novel Concept," Lucas Meyer Cosmetics, Total 6 pages, (May 2003).
Fukui, H., et al., "Isolation of Plant Growth Regulators form Seeds of *Cucurbita pepo* L.," Agricultural and Biological Chemistry, vol. 41, No. 1, pp. 175-180, (1977).
International Search Report Issued Mar. 29, 2012 in PCT/FR10/51372 Filed Jul. 1, 2010.

* cited by examiner

*Primary Examiner* — Marcos Sznaidman
(74) *Attorney, Agent, or Firm* — Oblon, McClelland, Maier & Neustadt, L.L.P.

(57) ABSTRACT

The invention relates to a method for cosmetically treating oily skin, including the topical application onto the skin of a composition containing a jasmonic acid compound in a physiologically acceptable medium.

14 Claims, No Drawings

USE OF A JASMONIC ACID COMPOUND FOR TREATING GREASY SKIN

The present invention relates to the cosmetic use of a jasmonic acid compound as an agent for making greasy skin matt.

The invention also relates to a cosmetic treatment process for making greasy skin matt, comprising the topical application to the skin of a composition containing, in a physiologically acceptable medium, a jasmonic acid compound.

Shiny skin is a problem most particularly affecting adolescents, but which may also appear in adulthood as a result especially of an overproduction of androgens. Shiny or greasy skin is generally a hyperseborrhoeic skin characterized by an exaggerated secretion and excretion of sebum, generally leading to a sebum level of greater than 200 µg/cm² measured on the forehead.

Sebum is the natural product of the sebaceous gland, which constitutes an annex of the pilosebaceous unit. It is essentially a more or less complex mixture of lipids. Conventionally, the sebaceous gland produces squalene, triglycerides, aliphatic waxes, cholesterol waxes and, possibly, free cholesterol (Stewart, M. E., *Semin. Dermatol.* 11, 100-105 (1992)). The action of bacterial lipases converts a variable proportion of the triglycerides formed into free fatty acids.

The sebocyte constitutes the competent cell of the sebaceous gland. The production of sebum is associated with a programme of terminal differentiation of this cell. During this differentiation, the metabolic activity of the sebocyte is essentially directed towards the biosynthesis of lipids (lipogenesis) and more precisely to fatty acid neosynthesis.

While sebum normally constitutes a natural moisturizer for the epidermis, the overproduction of sebum may lead to aesthetic problems, such as shiny skin, poorer hold of makeup, or the formation of comedones or blackheads.

To combat hyperseborrhoea, the prior art has thus proposed various compounds, which, by topical application to the skin, are capable of reducing the lipogenesis of the sebocytes and consequently of limiting the production of sebum.

Several cosmetic compositions capable of offering a solution to these problems have been proposed in the prior art. These compositions especially comprise as active principle powders for absorbing the sebum and thus making the skin matt via a mechanical effect.

However, there is still a need for cosmetic or dermatological compositions which can avoid the aesthetic problems associated with the overproduction of sebum, and which can especially avoid the bright appearance of greasy skin.

In this context, the Applicant proposes to use jasmonic acid derivatives of formula (I) in compositions, the said derivative and/or the said composition being intended to attenuate the cutaneous imperfections of greasy skin, and in particular being intended to attenuate the shiny, bright appearance of greasy skin.

The Applicant has now discovered that the use of jasmonic acid-based compounds makes it possible to formulate products that have good efficacy for treating greasy skin.

Such jasmonic acid compounds are known in patent application EP-A-1 333 021 for promoting desquamation of the skin. However, it was not suggested in that document that such compounds can have an effective action in the treatment of greasy skin, in particular for treating aesthetic disorders associated with an overproduction of sebum, and more particularly for making greasy skin matt.

One subject of the present invention is thus a cosmetic treatment process for making greasy skin matt, comprising the topical application to the skin, in particular greasy skin, of a composition comprising, in a physiologically acceptable medium, a compound of formula (I) as described below.

For the purposes of the present invention, the expression "cosmetic treatment of greasy skin" means the topical application of skincare products intended to reduce the sheen of the skin.

The invention also relates to the cosmetic use of a compound of formula (I) as described below as an agent for attenuating cutaneous imperfections of greasy skin, especially as an agent for making greasy skin matt.

The term "making matt" means making the skin visibly more matt and less shiny. The matting effect of the composition may especially be evaluated using a gonioreflectometer, by measuring the ratio R between the specular reflection and the scattered reflection. A value of R of less than or equal to 2 generally indicates a matting effect.

The composition used according to the invention is suitable for topical application to the skin and thus generally comprises a physiologically acceptable medium, i.e. a medium that is compatible with the skin.

The jasmonic acid-based compound is a compound chosen from those corresponding to formula (I) below:

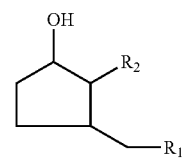

in which:

$R_1$ represents a radical $COOR_3$, $R_3$ denoting a hydrogen atom or a $C_1$-$C_4$ alkyl radical, optionally substituted with one or more hydroxyl groups;

$R_2$ represents a saturated or unsaturated linear hydrocarbon-based radical containing from 1 to 18 carbon atoms or a saturated or unsaturated branched or cyclic hydrocarbon-based radical containing from 3 to 18 carbon atoms;

and also the optical isomers thereof, and the corresponding salts.

Preferably, $R_1$ denotes a radical chosen from —COOH, —COOMe, —COO—CH$_2$—CH$_3$, —COO—CH$_2$—CH(OH)—CH$_2$OH, —COOCH$_2$—CH$_2$—CH$_2$OH and —COOCH$_2$—CH(OH)—CH$_3$. Preferentially, $R_1$ denotes a radical —COOH.

Preferentially, $R_2$ denotes a linear, saturated or unsaturated hydrocarbon-based radical, preferably containing from 2 to 7 carbon atoms. In particular, $R_2$ may be a pentyl, pentenyl, hexyl or heptyl radical.

According to one embodiment, the compound of formula (I) is chosen from 3-hydroxy-2-[(2Z)-2-pentenyl]cyclopentaneacetic acid and 3-hydroxy-2-pentylcyclopentaneacetic acid, and is preferably 3-hydroxy-2-pentylcyclopentaneacetic acid.

The salts of the compounds that may be used according to the invention are chosen in particular from salts of alkali metals, for example sodium or potassium; salts of alkaline-earth metals, for example calcium, magnesium or strontium; metal salts, for example zinc aluminium, manganese or copper; ammonium salts of formula $NH_4^{30}$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts. Salts chosen from sodium, potassium, magnesium, strontium, copper, manganese and zinc salts are preferably used.

The compound of formula (I) defined previously may be present in the used composition according to the invention in a content ranging from 0.01% to 10% by weight, and preferably from 0.1% to 5% by weight, relative to the total weight of the composition.

The composition according to the invention may comprise an additional matting agent.

The term "matting agent" means agents intended to make the skin visibly more matt and less shiny.

The matting agent may especially be chosen from a rice starch or a corn starch, kaolinite, silicas, talc, a pumpkin seed extract, cellulose microbeads, plant fibres, synthetic fibres, in particular polyamide fibres, expanded acrylic copolymer microspheres, polyamide powders, silica powders, polytetrafluoroethylene powders, silicone resin powders, acrylic copolymer powders, wax powders, polyethylene powders, powders of elastomeric crosslinked organopolysiloxane coated with silicone resin, talc/titanium dioxide/alumina/silica composite powders, amorphous mixed silicate powders, acrylic polymer powders, silicate particles and especially mixed silicate particles, and mixtures thereof.

Examples of matting agents that may especially be mentioned include:
- rice or corn starch, in particular an aluminium starch octenyl succinate sold under the name Dry Flo® by the company National Starch;
- kaolinite;
- silicas;
- talc;
- a pumpkin seed extract as sold under the name Curbilene® by the company Indena;
- cellulose microbeads as described in L'Oréal patent application EP 1 562 562;
- fibres, such as silk fibre, cotton fibre, wool fibre, flax fibre, cellulose fibre extracted especially from wood, from vegetables or from algae, polyamide fibre (Nylon®), modified cellulose fibre, poly-p-phenyleneterephthamide fibre, acrylic fibre, polyolefin fibre, glass fibre, silica fibre, aramid fibre, carbon fibre, Teflon® fibre, insoluble collagen fibre, polyester fibre, polyvinyl chloride or polyvinylidene chloride fibre, polyvinyl alcohol fibre, polyacrylonitrile fibre, chitosan fibre, polyurethane fibre, polyethylene phthalate fibre, fibres formed from a mixture of polymers, resorbable synthetic fibres, and mixtures thereof described in L'Oréal patent application EP 1 151 742;
- expanded acrylic copolymer microspheres such as those sold by the company Expancel under the name Expancel 551®;
- fillers with an optical effect as described in patent application FR 2 869 796, in particular:
  - polyamide powders (Nylon®), for instance Nylon 12 particles of the Orgasol type from Atofina, with a mean size of 10 microns and a refractive index of 1.54,
  - silica powders, for instance Silica beads SB150 from Miyoshi with a mean size of 5 microns and a refractive index of 1.45,
  - polytetrafluoroethylene powders, for instance PTFE Ceridust 9205F from Clariant, with a mean size of 8 microns and a refractive index of 1.36,
  - silicone resin powders, for instance the silicone resin Tospearl 145A from GE Silicone with a mean size of 4.5 microns and a refractive index of 1.41,
  - acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku,
  - wax powders, for instance the paraffin wax particles Microease 114S from Micropowders, with a mean size of 7 microns and a refractive index of 1.54,
  - polyethylene powders, especially comprising at least one ethylene/acrylic acid copolymer, and in particular consisting of ethylene/acrylic acid copolymers, for instance the particles Flobeads EA 209 from Sumitomo (with a mean size of 10 microns and a refractive index of 1.48),
  - elastomeric crosslinked organopolysiloxane powders coated with silicone resin, especially with silsesquioxane resin, as described, for example, in U.S. Pat. No. 5,538,793. Such elastomer powders are sold under the names KSP-100, KSP-101, KSP-102, KSP-103, KSP-104 and KSP-105 by the company Shin-Etsu, and
  - talc/titanium dioxide/alumina/silica composite powders such as those sold under the name Coverleaf AR-80 by the company Catalyst & Chemicals,
- and mixtures thereof,
- compounds that absorb and/or adsorb sebum as described in the same patent application FR 2 869 796. Mention may be made especially of:
  - silica powders, for instance the porous silica microspheres sold under the name Silica Beads SB-700 sold by the company Miyoshi, the products Sunsphere® H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass;
  - amorphous mixed silicate powders, especially of aluminium and magnesium, for instance the product sold under the name Neusilin UFL2 by the company Sumitomo;
  - polyamide (Nylon®) powders, for instance Orgasol® 4000 sold by the company Atochem, and
  - acrylic polymer powders, especially of polymethyl methacrylate, for instance Covabead® LH85 sold by the company Wackherr; of polymethyl methacrylate/ethylene glycol dimethacrylate, for instance Dow Corning 5640 Microsponge® Skin Oil Adsorber sold by the company Dow Corning, or Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;
  - silicate particles, such as alumina silicate;
  - mixed silicate particles, such as:
    - magnesium aluminium silicate particles, such as saponite or hydrated magnesium aluminium silicate with a sodium sulfate sold under the trade name Sumecton® by the company Kunimine;
    - the magnesium silicate, hydroxyethylcellulose, black cumin oil, marrow oil and phospholipids complex or Matipure® from Lucas Meyer,
- and mixtures thereof.

Preferred matting agents that may be used according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

The compositions according to the invention are preferentially cosmetic compositions for caring for greasy skin.

These compositions are intended for topical application to the face and/or the body. In particular, the composition is applied to the areas of the face or the forehead presenting shiny skin.

They may also be shaving or aftershave compositions, in particular for men.

The compositions according to the invention may be provided in all the formulation forms conventionally used for a topical application and in particular in the form of aqueous or aqueous/alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, lipid vesicles of ionic and/or nonionic type (liposomes, niosomes or oleosomes), or thin films. These compositions are prepared according to the usual methods.

According to one preferred embodiment of the invention, the composition is in the form of an oil-in-water emulsion or an aqueous gel.

In addition, the compositions used according to the invention may be more or less fluid and may have the appearance of a white or coloured cream, a pomade, a milk, a lotion, a serum, a paste or a mousse. They may optionally be applied to the skin in aerosol form. They may also be in solid form, for example in stick form.

Such a composition may be a care composition, an exfoliant, cleansing or scrubbing composition, or a shaving composition such as a shaving foam.

When the composition used according to the invention comprises an oily phase, it preferably contains at least one oil. It may also contain other fatty substances.

As oils that may be used in the composition of the invention, examples that may be mentioned include:
  hydrocarbon-based oils of animal origin, such as perhydrosqualene;
  hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, sun-flower oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;
  synthetic esters and ethers, especially of fatty acids, for instance the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;
  linear or branched hydrocarbons of mineral or synthetic origin, such as volatile or non-volatile liquid paraffins, and derivatives thereof, petroleum jelly, polydecenes, and hydrogenated polyisobutene such as Parleam oil;
  fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;
  partially hydrocarbon-based and/or silicone-based fluoro oils, for instance those described in document JP-A-2 295 912;
  silicone oils, for instance volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenylsilicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;
  mixtures thereof.

In the list of oils mentioned above, the term "hydrocarbon-based oil" means any oil mainly comprising carbon and hydrogen atoms, and possibly ester, ether, fluoro, carboxylic acid and/or alcohol groups.

In this case, the proportion of emulsion in the fatty phase may range, for example, from 1% to 40% by weight relative to the total weight of the composition. The oils, emulsifiers and coemulsifiers used in the composition in emulsion form are chosen from those conventionally used in cosmetics or dermatology. The emulsifier and the co-emulsifier are generally present in the composition in a proportion ranging from 0.3% to 30% by weight and preferably from 0.5% to 20% by weight relative to the total weight of the composition.

In the case where the composition according to the invention is in the form of an O/W emulsion, it may contain, as surfactants, at least one compound chosen from: esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylene and/or oxypropylene units, such as the glyceryl esters of $C_8$-$C_{24}$ fatty acids, and the oxyalkylenated derivatives thereof; sorbitol esters of $C_8$-$C_{24}$ fatty acids, and the oxyalkylenated derivatives thereof; sugar (sucrose, glucose or alkylglucose) esters of $C_8$-$C_{24}$ fatty acids, and the oxyalkylenated derivatives thereof; polyethylene glycol esters of $C_8$-$C_{24}$ fatty acids, and the oxyalkylenated derivatives thereof; $C_8$-$C_{24}$ fatty alkyl ethers of polyalkylene glycols; $C_8$-$C_{24}$ fatty alkyl ethers of sugars, and mixtures thereof.

The composition according to the invention may also contain adjuvants that are common in cosmetics and dermatology, such as hydrophilic or lipophilic gelling agents, active agents, preserving agents, solvents, fragrances, fillers, pigments, odour absorbers and dyestuffs. The amounts of these various adjuvants are those conventionally used in the field under consideration, for example from 0.01% to 20% of the total weight of the composition. Depending on their nature, these adjuvants may be introduced into the fatty phase or into the aqueous phase. These adjuvants and the concentrations thereof should be such that they do not modify the advantageous properties of the cellulose microbeads according to the invention.

The invention will now be illustrated with the aid of the non-limiting examples that follow. In these examples, unless otherwise indicated, the amounts are indicated as weight percentages.

EXAMPLE 1

Demonstration of the Activity of 3-Hydroxy-2-Pentylcyclopentaneacetic Acid on Greasy Skin An in vivo panel test was performed with a cosmetic composition comprising 3-hydroxy-2-pentylcyclopentaneacetic acid, and revealed the efficacy of the compound for treating greasy skin.

EXAMPLE 2

A facial care composition is prepared, comprising the following ingredients (weight percentages):

| | |
|---|---|
| 3-Hydroxy-2-pentylcyclopentaneacetic acid | 1% |
| Propylene glycol isostearate | 13% |
| Polyethylene glycol (8 OE) | 5% |
| Propylene glycol | 3% |
| Pentylene glycol | 3% |
| Glyceryl stearate and polyethylene glycol stearate (100 OE) | 5% |
| Oxyethylenated (20 OE) sorbitan monostearate | 0.5% |
| Oxyethylenated (20 OE) and oxypropylenated (5 OP) cetyl alcohol | 1% |
| Gelling agents | 0.5% |
| $C_{12-15}$ alkyl benzoates | 4% |
| Ethanol | 3% |
| Sodium hydroxide | 0.12% |
| Preserving agents | 0.7% |
| Water qs | 100% |

This fluid is intended to be used in applications once or twice daily on the face and the forehead, for attenuating the greasy appearance of the skin.

The invention claimed is:

1. A method for mattifying oily skin, the method comprising:
contacting oily skin in need of mattifying with a composition comprising a compound of formula (I)

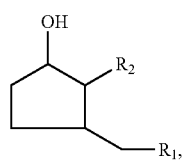

(I)

wherein
$R_1$ is a radical $COOR_3$, $R_3$ is a hydrogen atom or a $C_1$-$C_4$ alkyl radical, optionally substituted with at least one hydroxyl group; and
$R_2$ is a saturated linear hydrocarbon radical comprising from 1 to 18 carbon atoms or a saturated branched or cyclic hydrocarbon-based radical comprising from 3 to 18 carbon atoms,
or an optical isomer or a salt of the compound of formula (I), wherein said contacting oily skin is effective in mattifying the skin.

2. The process of claim 1, wherein
$R_1$ is a radical selected from the group consisting of from —COOH, —COOMe, —COO—CH$_2$—CH$_3$, —COO—CH$_2$—CH(OH)—CH$_2$OH, —COOCH$_2$—CH$_2$—CH$_2$OH, and —COOCH$_2$—CH(OH)—CH$_3$, and
$R_2$ is a saturated linear hydrocarbon radical comprising from 2 to 7 carbon atoms.

3. The process of claim 1, wherein the compound of formula (I) is 3-hydroxy-2-pentylcyclopentaneacetic acid.

4. The process of claim 1, wherein a content of the compound of formula (I) in the composition is from 0.01% to 10% by weight based on a total weight of the composition.

5. The process of claim 1, wherein a content of the compound of formula (I) in the composition is from 0.1% to 5% by weight based on a total weight of the composition.

6. The process of claim 1, wherein the composition is in the form of an oil-in-water emulsion or an aqueous gel.

7. The process of claim 1, wherein the skin is hyperseborrhoeic skin.

8. A method for reducing the sheen of greasy skin, the method comprising:
contacting greasy skin in need of sheen reduction with a composition comprising a compound of formula (I)

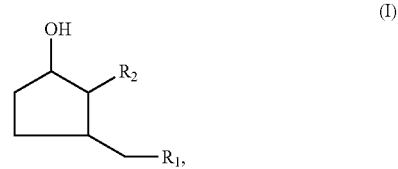

(I)

wherein
$R_1$ is a radical $COOR_3$, $R_3$ is a hydrogen atom or a $C_1$-$C_4$ alkyl radical, optionally substituted with at least one hydroxyl group; and
$R_2$ is a saturated linear hydrocarbon radical comprising from 1 to 18 carbon atoms or a saturated branched or cyclic hydrocarbon-based radical comprising from 3 to 18 carbon atoms,
or an optical isomer or a salt of the compound of formula (I), wherein said contacting greasy skin is effective in reducing sheen of the skin.

9. The method of claim 8, wherein
$R_1$ is a radical selected from the group consisting of from —COOH, —COOMe, —COO—CH$_2$—CH$_3$, —COO—CH$_2$—CH(OH)—CH$_2$OH, —COOCH$_2$—CH$_2$—CH$_2$OH, and —COOCH$_2$—CH(OH)—CH$_3$, and
$R_2$ is a saturated linear hydrocarbon radical comprising from 2 to 7 carbon atoms.

10. The method of claim 8, wherein the compound of formula (I) is 3-hydroxy-2-pentylcyclopentaneacetic acid.

11. The method of claim 8, wherein a content of the compound of formula (I) in the composition is from 0.01% to 10% by weight based on a total weight of the composition.

12. The method of claim 8, wherein a content of the compound of formula (I) in the composition is from 0.1% to 5% by weight based on a total weight of the composition.

13. The method of claim 8, wherein the composition is in the form of an oil-in-water emulsion or an aqueous gel.

14. The method of claim 8, wherein the skin is hyperseborrhoeic skin.

\* \* \* \* \*